United States Patent [19]

Hartwig

[11] Patent Number: 4,847,287
[45] Date of Patent: Jul. 11, 1989

[54] PURE ENANTIOMERS OF 4,5-DISUBSTITUTED GAMMA-BUTYROLACTAMS, AND THEIR USE AS ANTIAMNESTIC AGENTS

[75] Inventor: Wolfgang Hartwig, Wuppertal, Fed. Rep. of Germany

[73] Assignees: Bayer AG, Leverkusen, Fed. Rep. of Germany; Chinese Academy of Medical Sciences, Beijing, China

[21] Appl. No.: 50,604

[22] Filed: May 14, 1987

[30] Foreign Application Priority Data

May 21, 1986 [DE] Fed. Rep. of Germany ....... 3616989

[51] Int. Cl.$^4$ .................... A61K 31/40; C07D 207/08; C07D 207/12
[52] U.S. Cl. ................................. 514/423; 548/532; 548/533; 548/534
[58] Field of Search ............... 548/332, 533, 534, 532; 514/255, 423

[56] References Cited

U.S. PATENT DOCUMENTS 3,178,347 4/1965 Bocher ............................ 548/534
4,296,110 10/1981 Johnson ........................... 548/534
4,731,455 3/1988 Hartwig ........................... 548/534

FOREIGN PATENT DOCUMENTS 0172514 2/1986 European Pat. Off. .
3632589 4/1987 Fed. Rep. of Germany .

OTHER PUBLICATIONS

Burger, Medicinal Chemistry, 2nd Edition, 1960, pp. 42–43.

Hartwig et al., Chem. Abst. vol. 95 (1981) 62704c.
Chemische Berichte, Jahrgang 100, Heft 4, 1967, Seiten 1137–1143 F. Zymalkowski et al.: "Eine Stereoselektive Synthese von Cisund Trans-3-Phenyl-2-Carboxy-Pyrrolidon-(5)", *Seite 1138, Beispiel 2b$_2$*.
Synthesis, Nr. 9, Sep. 1986, Seiten 737–740 U. Schollkopf et al.: "Assymmetric Synthesis via Heterocyclic Intermediates. XXX. Assymmetric Synthesis of Glutamic Acids and Derivatives thereof by the Bislactim-Ether Method. Michael-Addtion of Methyl 2-Alkenoates to the Lithiated Bislactim-Ether of Cyclo-(-L-Val-Gly)", *Insgesamt*.

Primary Examiner—Anton H. Sutto
Assistant Examiner—Cecilia Shen
Attorney, Agent, or Firm—Sprung Horn Kramer et al.

[57] ABSTRACT

The invention provides pure enatiomers of 4,5-disubstituted γ-butyrolactams of the general formula

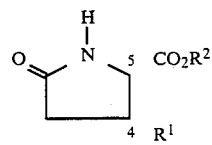

By means of the pure enantiomers of 4,5-disubstituted γ-butyrolactams (I), according to the invention, it is now possible to synthesize (+)-(3R), (4S), (5S), (7R)-3-hydroxy-5-α-hydroxybenzyl-1-methyl-4-phenyl-pyrrolidin-2-one and derivatives in the form of pure enantiomers.

5 Claims, No Drawings

PURE ENANTIOMERS OF 4,5-DISUBSTITUTED GAMMA-BUTYROLACTAMS, AND THEIR USE AS ANTIAMNESTIC AGENTS

The invention relates to pure enantiomers of 4,5-disubstituted γ-butyrolactams, to a process for their preparation and to their use as intermediates for pharmaceutical active compounds.

The invention provides pure enantiomers of 4,5-disubstituted γ-butyrolactams of the general formula (I)

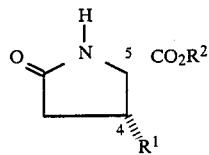

in which $R^1$ represents aryl which has 6 to 14 carbon atoms and which can be up to pentasubstituted by identical or different substituents selected from the group consisting of alkyl, alkoxy and alkylthio each having up to 8 carbon atoms, aryl, aryloxy and arylthio each having 6 to 12 carbon atoms, aralkyl having 7 to 14 carbon atoms, halogen, trifluoromethyl, trifluoromethoxy, difluoromethoxy, trifluoromethylthio, nitro, cyano, carboxyl, alkoxycarbonyl having up to 8 carbon atoms, sulpho, phenylsulphonyl, tolylsulphonyl, alkylsulphonyl having up to 8 carbon atoms, hydroxyl or a group of the formula

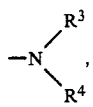

wherein $R^3$ and $R^4$ are identical or different and denote hydrogen, alkyl having up to 8 carbon atoms, aryl having 6 to 12 carbon atoms, aralkyl having 7 to 14 carbon atoms, acyl having up to 7 carbon atoms, alkylsulphonyl having up to 6 carbon atoms, phenylsulfonyl or tolylsulfonyl, or represents a heterocyclic ring from the group comprising furyl, thienyl, pyridyl, pyrimidyl, pyrazinyl, pyridazinyl, quinolyl or isoquinolyl, it being possible for these rings to be up to trisubstituted by identical or different substituents selected from the group consisting of alkyl, alkoxy and alkylthio each having up to 6 carbon atoms, halogen, phenyl, nitro, cyano and a group of the formula

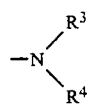

wherein $R^3$ and $R^4$ have the meaning given above, or represents straight-chain, branched or cyclic alkyl or alkenyl which have up to 10 carbon atoms and can be substituted by halogen, aryl having 6 to 14 carbon atoms, furyl, thienyl, pyridyl, pyrimidyl, pyrazinyl, pyridazinyl, quinolyl, isoquinolyl, hydroxyl, alkoxy and alkylthio each having up to 6 carbon atoms, carboxyl, alkoxycarbonyl having up to 6 carbon atoms, sulfo, alkylsulfonyl having up to 6 carbon atoms, phenylsulfonyl, tolylsulfonyl or by a group of the formula

wherein $R^5$ and $R^6$ are identical or different and denote hydrogen, alkyl having up to 8 carbon atoms, aryl having 6 to 12 carbon atoms, aralkyl having 7 to 14 carbon atoms, acyl having up to 7 carbon atoms, alkylsulfonyl having up to 6 carbon atoms, phenylsulfonyl or tolylsulfonyl, or wherein $R^5$ and $R^6$ together with the nitrogen atom form a ring from the group comprising pyrrolidino, piperidino, piperazino, morpholino and thiomorpholino, it being possible for this ring to be substituted by alkyl having up to 4 carbon atoms or by phenyl, and $R^2$ represents straight-chain, branched or cyclic alkyl having up to 8 carbon atoms, and in which the ring carbon atom at the 5-position has the S-configuration and wherein the substituent $R^1$ in the 4-position has the cis-configuration relative to the substituent $COOR^2$ in the 5-position.

Preferred compounds of the general formula (I) are those in which $R^1$ represents phenyl or naphthyl which can be up to trisubstituted by identical or different substituents selected from the group consisting of alkyl and alkoxy each having up to 6 carbon atoms, methylthio, phenyl, phenoxy, benzyl, fluoro, chloro, bromo, iodo, trifluoromethyl, trifluoromethoxy, difluoromethoxy, trifluoromethylthio, nitro, cyano, alkoxycarbonyl having up to 6 carbon atoms, phenylsulfonyl, tolylsulfonyl, alkylsulfonyl having up to 6 carbon atoms, hydroxyl and a group of the formula

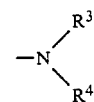

in which $R^3$ and $R^4$ are identical or different and denote hydrogen, alkyl having up to 6 carbon atoms, phenyl, benzyl, acetyl, ethylcarbonyl, benzoyl, alkylsulfonyl having up to 4 carbon atoms, tolylsulfonyl or phenylsulfonyl, or represents a heterocyclic ring from the group comprising furyl, thienyl, pyridyl, pyrimidyl, quinolyl and isoquinolyl, it being possible for these rings to be substituted by alkyl or alkoxy having up to 4 carbon atoms, by fluoro, chloro, bromo, nitro, cyano or by a group of the formula

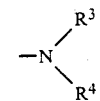

wherein
R³ and R⁴ have the meaning given above,
or represents a straight-chain, branched or cyclic alkyl which has up to 8 carbon atoms and which can be substituted by fluoro, chloro, bromo, phenyl, furyl, thienyl, pyridyl, pyrimidyl, quinolyl, isoquinolyl, hydroxyl, alkoxy or alkylthio having up to 4 carbon atoms, alkoxycarbonyl having up to 4 carbon atoms, alkylsulfonyl having up to 4 carbon atoms, phenylsulfonyl, tolylsulfonyl or by a group of the formula

wherein
R⁵ and R⁶ are identical or different and denote hydrogen, alkyl having up to 6 carbon atoms, phenyl, benzyl, acetyl, ethylcarbonyl, benzoyl, alkylsulfonyl having up to 4 carbon atoms, tolylsulfonyl or phenylsulfonyl or
in which R⁵ and R⁶ together with a nitrogen atom form a ring from the group comprising pyrrolidino, piperidino, N-methyl- or N-phenyl-piperazino or morpholino,
and R² represents straight-chain or branched alkyl having up to 6 carbon atoms, and in which the ring carbon atom at the 5-position has the S-configuration and in which the substituent R¹ in the 4-position has the cis-configuration relative to the substituent COOR² in the 5-position.

Particularly preferred are those compounds of the general formula (I)
in which
R¹ represents phenyl which can be substituted by alkyl or alkoxy having up to 4 carbon atoms, by fluoro, chloro, bromo, trifluoromethyl, trifluoromethoxy, trifluoromethylthio, nitro, cyano, alkoxycarbonyl having up to 4 carbon atoms, phenylsulfonyl, tolylsulfonyl, alkylsulfonyl having up to 4 carbon atoms, hydroxyl or by a group of the formula

in which
R³ and R⁴ are identical or different and denote hydrogen, alkyl, having up to 4 carbon atoms, phenyl, benzyl or acetyl,
or represents furyl, thienyl or pyridyl, or represents straight-chain, branched or cyclic alkyl which has up to 6 carbon atoms and can be substituted by fluoro, chloro, bromo, phenyl, thienyl, pyridyl, furyl or alkoxy having up to 4 carbon atoms
and R² represents straight-chain or branched alkyl having up to 4 carbon atoms, and in which the ring carbon atom at the 5-position has the S-configuration and in which the substituent R¹ in the 4-position has the cis-configuration relative to the substituent COOR² in the 5-position.

Likewise, a process has been found for the preparation of pure enantiomers of 4,5-disubstituted γ-butyrolactams of the general formula (I)
in which R¹ represents aryl which has 6 to 14 carbon atoms and which can be up to pentasubstituted by identical or different substituents selected from the group consisting of alkyl, alkoxy and alkylthio each having up to 8 carbon atoms, aryl, aryloxy and arylthio each having 6 to 12 carbon atoms, aralkyl having 7 to 14 carbon atoms, halogen, trifluoromethyl, trifluoromethoxy, difluoromethoxy, trifluoromethylthio, nitro, cyano, carboxyl, alkoxycarbonyl having up to 8 carbon atoms, sulfo phenylsulfonyl, tolylsulfonyl, alkylsulfonyl having up to 8 carbon atoms, hydroxyl or a group of the formula

wherein
R³ and R⁴ are identical or different and denote hydrogen, alkyl having up to 8 carbon atoms, aryl having 6 to 12 carbon atoms, aralkyl having 7 to 14 carbon atoms, acyl having 2 to 7 carbon atoms, alkylsulfonyly having up to 6 carbon atoms, phenylsulfonyl or tolylsulfonyl
or represents a heterocyclic ring from the group comprising furyl, thienyl, pyridyl, pyrimidyl, pyrazinyl, pyridazinyl, quinolyl or isoquinolyl, it being possible for these rings to be up to trisubstituted by identical or different substituents selected from the group consisting of alkyl, alkoxy and alkylthio each having up to 6 carbon atoms, halogen, phenyl, nitro, cyano and a group of the formula

wherein
R³ and R⁴ have the meaning given above,
or represents straight-chain, branched or cyclic alkyl or alkenyl which have up to 10 carbon atoms and can be substituted by halogen, aryl having 6 to 14 carbon atoms, furyl, thienyl, pyridyl, pyrimidyl, pyrazinyl, pyridazinyl, quinolyl, isoquinolyl, hydroxyl, alkoxy and alkylthio each having up to 6 carbon atoms, carboxyl, alkoxycarbonyl having up to 6 carbon atoms, sulfo, alkylsulfonyl having up to 6 carbon atoms, phenylsulfonyl tolylsulfonyl or by a group of the formula

wherein
R⁵ and R⁶ are identical or different and denote hydrogen, alkyl having up to 8 carbon atoms, aryl having 6 to 12 carbon atoms, aralkyl having 7 to 14 carbon atoms, acyl having up to 7 carbon atoms, alkylsulfonyl having up to 6 carbon atoms, phenylsulfonyl or tolylsulfonyl
or wherein
R⁵ and R⁶ together with the nitrogen atom form a ring from the group comprising pyrrolidino, piperidino, piperazino, morpholino and thiomorpholino, it being possible for this ring to be substituted by alkyl having up to 4 carbon atoms or by phenyl, and $R^2$ represents straight-chain, branched or cyclic alkyl having up to 8 carbon atoms, and in which the ring carbon atom at the 5-position has the S-configuration and wherein the substituent $R^1$ in the 4-position has the cis-configuration relative to the substituent $COOR^2$ in the 5-position, which process is characterized in that dihydropyrazines of the formula (II)

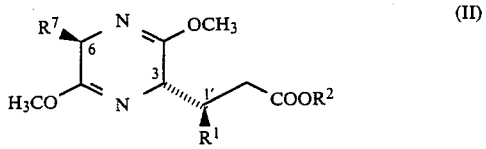

in which $R^1$ and $R^2$ have the meaning given above and $R^7$ represents straight-chain or branched alkyl having up to 4 carbon atoms, the carbon atom 6 of the dihydropyrazine ring in II has the R-configuration, the carbon atom 3 of the pyrazine ring in (II) has the S-configuration and the carbon atom at 1' has the S-configuration, if $R^1$ has a higher priority than the group $CH_2COOR^2$, or has the R-configuration, if $R^1$ has lower priority than the group $CH_2COOR^2$, are first hydrolyzed with acids in inert solvents, then the free amino acids are prepared from the resulting acidic amino acid salts with bases in inert solvents and the free acids are subsequently cyclized.

When (3S,6R,1'S)-2,5-dimethoxy-6-isopropyl-3-(2'-methoxycarbonyl-1'-phenyl)-ethyl-3,6-dihydro-1,4-pyrazine is used as the starting material, the process can be illustrated by the following equation:

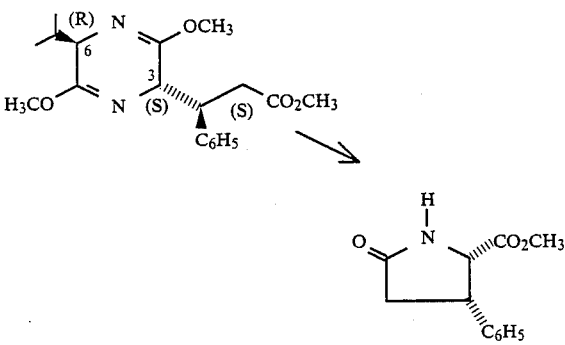

(1.) Acid
(2.) Base
(3.) Cyclization

Suitable solvents are the conventional inert solvents which do not change under the reaction conditions. These include, preferably, water or alcohols, such as, for example, methanol, ethanol, propanol or isopropanol, or ethers, such as, for example, diethyl ether, dioxane or tetrahydrofuran, or chlorohydrocarbons, such as, for example, methylene chloride, chloroform or carbon tetrachloride, or also mixtures of the solvents mentioned.

Suitable acids for the hydrolysis are inorganic acids, such as, for example, hydrochloric acid, hydrobromic acid, sulfuric acid or phosphoric acid, or organic carboxylic or sulfonic acids, such as, for example, methane-, ethane-, toluene- or benzene-sulfonic acid or acetic acid or propionic acid.

Particularly preferably, the hydrolysis is carried out in aqueous or alcoholic solutions with hydrogen chloride as the acid.

The hydrolysis is in general carried out at a temperature from 0° C. to +100° C., preferably from +20° C. to +60° C.

In general, the process is carried out under normal pressure. However, the process can also be carried out under an elevated or reduced pressure.

The glutamic acid salts obtained in the hydrolysis can be isolated. However, a direct further processing of the amino acid salts without purification has here proven to be advantageous.

For liberating the amino acid, the salts are treated with bases in an inert solvent.

Suitable solvents are here the conventional inert solvents which do not change under the reaction conditions. These include, preferably, water or alcohols, such as, for example, methanol, ethanol, propanol or isopropanol, or ethers, such as diethyl ether, dioxane or tetrahydrofuran, acetonitrile, dimethylformamide or hexamethylphosphoric acid triamide or mixtures of the solvents mentioned.

Suitable bases are the conventional basic compounds. These include, preferably, inorganic bases, such as alkali metal or alkaline earth metal hydroxides, for example sodium hydroxide, potassium hydroxide, calcium hydroxide or barium hydroxide, or alkali metal carbonates, such as sodium carbonate, sodium bicarbonate or potassium carbonate, or ammonia, or organic amines derived from ammonia, such as di- or tri-alkylamines, for example triethylamine or diisopropylamine, or other tertiary amines, such as, for example, pyridine, dimethylaminopyridine, picoline or lutidine.

Preferably, ammonia or triethylamine in aqueous or alcoholic solutions are used as the bases.

The treatment of the amino acid salts with bases is in general carried out in a temperature range from 0° C. to +100° C., preferably from +20° C. to +40° C.

The reaction is in general carried out under normal pressure. It is also possible to carry out the process under an elevated or reduced pressure.

The free amino acids can be isolated. In general, however, a direct further processing without isolation of the amino acid has proved to be advantageous.

The cyclization of the free amino acid is in general carried out without a solvent in a temperature range from +50° C. to +200° C., preferably from +70° C. to +120° C.

The cyclization can be carried out under normal pressure, under an elevated pressure or under a reduced pressure. In general, normal pressure is used.

The process according to the invention can be carried out, for example, in such a way that the dihydropyrazines are treated with aqueous hydrochloric acid, the resulting glutamic acid salts are then isolated and, without purification, treated with aqueous ammonia, and the free amino acids are then isolated and heated without a solvent, for example in a bulb tube.

The dihydropyrazines, used as starting materials, of the general formula (II)

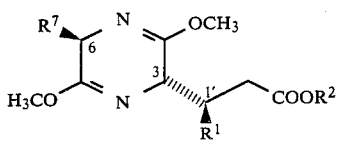

in which

R¹ represents aryl having 6 to 14 carbon atoms and which can be up to pentasubstituted by identical or different substituents selected from the group consisting of alkyl, alkoxy and alkylthio each having up to 8 carbon atoms, aryl, aryloxy and arylthio each having 6 to 12 carbon atoms, aralkyl having 7 to 14 carbon atoms, halogen, trifluoromethyl, trifluoromethoxy, difluoromethoxy, trifluoromethylthio, nitro, cyano, carboxyl, alkoxycarbonyl having up to 8 carbon atoms, sulfo, phenylsulfonyl, tolylsulfonyl, alkylsulfonyl having up to 8 carbon atoms, hydroxyl or a group of the formula

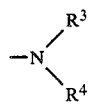

wherein

R³ and R⁴ are identical or different and denote hydrogen, alkyl having up to 8 carbon atoms, aryl having 6 to 12 carbon atoms, aralkyl having 7 to 14 carbon atoms, acyl having 2 to 7 carbon atoms, alkylsulfonyl having up to 6 carbon atoms, phenylsulfonyl or tolylsulfonyl or represents a heterocyclic ring from the group comprising furyl, thienyl, pyridyl, pyrimidyl, pyrazinyl, pyridazinyl, quinolyl or isoquinolyl, it being possible for these rings to be up to trisubstituted by identical or different substituents selected from the group consisting of alkyl, alkoxy and alkylthio each having up to 6 carbon atoms, halogen, phenyl, nitro, cyano and a group of the formula

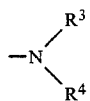

wherein

R³ and R⁴ have the meaning given above, or represents straight-chain, branched or cyclic alkyl or alkenyl which have up to 10 carbon atoms and can be substituted by halogen, aryl having 6 to 14 carbon atoms, furyl, thienyl, pyridyl, pyrimidyl, pyrazinyl, pyridazinyl, quinolyl, isoquinolyl, hydroxyl, alkoxy and alkylthio each having up to 6 carbon atoms, carboxyl, alkoxycarbonyl having up to 6 carbon atoms, sulfo, alkylsulfonyl having up to 6 carbon atoms, phenylsulfonyl, tolylsulfonyl or by a group of the formula

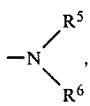

wherein

R⁵ and R⁶ are identical or different and denote hydrogen, alkyl having up to 8 carbon atoms, aryl having 6 to 12 carbon atoms, aralkyl having 7 to 14 carbon atoms, acyl having up to 7 carbon atoms, alkylsulfonyl having up to 6 carbon atoms, phenylsulfonyl or tolylsulfonyl, or wherein R⁵ and R⁶ together with the nitrogen atom form a ring from the group comprising pyrrolidino, piperidino, piperazino, morpholino and thiomorpholino, it being possile for this ring to be substituted by alkyl having up to 4 carbon atoms or by phenyl, R² represents straight-chain, branched or cyclic alkyl having up to 8 carbon atoms, and R⁷ represents straight-chain or branched alkyl having up to 4 carbon atoms, and wherein the carbon atom 3 of the dihydropyrazine ring has the S-configuration and the carbon atom 6 has the R-configuration, and the carbon atom 1 of the side chain has the S-configuration, if R¹ has a higher priority than the group CH₂COOR², or has the R-configuration, if R¹ has a lower priority than the group CH₂COOR², are novel and can be prepared by reacting compounds of the general formula (III)

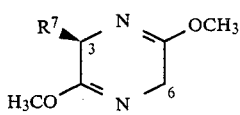

in which

R⁷ has the meaning given above and the carbon atom 3 of the dihydropyrazine ring has the R-configuration, first with a strongly basic metal-organic compound to give derivatives of (III) which are monosubstituted in the 6-position by the metal of the metal-organic compounds, then reacting these metal derivatives in inert solvents with a cis-substituted acrylic ester of the general formula (IV)

in which

R¹ and R² have the meaning given above, and finally neutralizing with an acid.

It is known from DOS (German Published Specification) No. 2,934,252 that pure enantiomers of 2-amino acids of serines are obtained from lactim ethers of type III by alkylation or reaction with carbonyl compounds.

It is also known [Chem. Scripta 25, 105 (1985)] that lactim ethers of type (III) give, with trans-substituted α,β-unsaturated carboxylic acid esters, 2,3-threoamino acids and, from these, 4,5-trans-substituted γ-butyrolactams.

In the light of knowledge of the state of the art, it was not to be expected that cis-substituted α,β-unsaturated carboxylic acid esters of type (IV) would selectively react with lactim ethers of type (III) to give pure enantiomers of the dihydropyrazines of type (II), which in turn represent precursors for the pure enantiomers of γ-butyrolactams, having the cis-configuration, of the formula (I).

When (3R)-2,5-dimethoxy-3-isopropyl-3,6-dihydro-1,4-pyrazine and methyl cis-cinnamate are used as the starting materials, the process can be illustrated by the following equation:

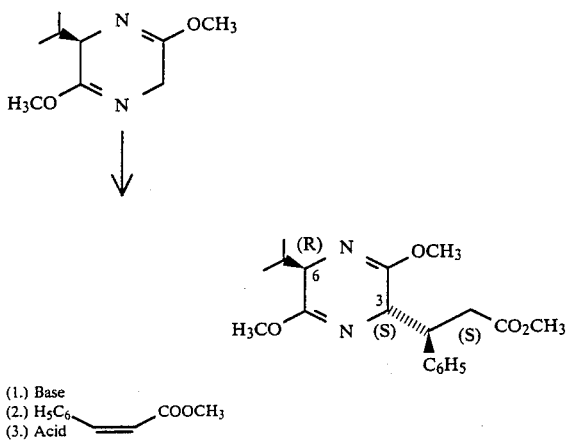

(1.) Base
(2.) H₅C₆—COOCH₃
(3.) Acid

The compounds of the general formula (III), employed as the starting materials, are known (DOS (German Published Specification) No. 2,934,252).

The acrylic esters of the general formula (IV), used as starting materials, are known or can be prepared by known methods (see, for example, Houben-Weyl, "Methoden der organischen Chemie" [Methods of Organic Chemistry]", 4th edition, volume 5/1b, pages 728 et seq.].

Suitable solvents are the conventional inert organic solvents which do not change under the reaction conditions. These include, preferably, ethers, such as diethyl ether, tetrahydrofuran, dioxane, glycol mono- or dimethyl ether, or amides such as dimethylformamide, hexamethyl phosphoric acid triamide or dimethylacetamide, or dimethyl sulfoxide. It is also possible to use mixtures of the solvents mentioned.

Suitable strongly basic metal-organic compounds are the conventional alkali metal-organic compounds. These include, preferably, alkali metal alcoholates such as sodium methylate, potassium methylate, sodium ethylate, potassium ethylate or potassium tert-butylate, or lithium-organic compounds such as n-, iso- or tert-butyllithium or phenyllithium, or alkali metal amides such as, for example, sodium amide, lithium diisopropylamide, lithium tetramethylpiperidide or sodium bis(trimethylsilyl)-amide.

Suitable acids for neutralization are the conventional inorganic or organic acids. These include, preferably, inorganic acids such as hydrochloric acid, hydrobromic acid, sulfuric acid or phosphoric acid, or organic carboxylic or sulfonic acids, such as acetic acid, propionic acid, tartaric acid or citric acid and methane sulfonic acid or ethane sulfonic acid.

The process is in general carried out in a temperature range from −80° C. to 0° C., preferably from −70° C. to −20° C.

The process is in general carried out under normal pressure. It is also possible for it to be carried out under an elevated or reduced pressure.

If, instead of the 2,5-dimethoxy-3-isopropyl-3,6-dihydro-1,4-pyrazine having the R-configuration at carbon atom 3, the corresponding S-enantiomer is used as the starting material, compounds II having the (6S),(3R),(1′R)-configuration are formed, as expected.

The pure enantiomers of 4,5-disubstituted γ-butyrolactams, according to the invention, of the formula (I) are valuable intermediates for pharmaceutical active compounds.

It is known, for example from European Patent specification 172,514, that Clausen amide [(±)−(3S*),(4R*),(5R*), (7S*)-3-hydroxy-α-hydroxybenzyl-1-methyl-4-phenylpyrrolidin-2-one] which is isolated from the aqueous extract from *Clausena lansium* (lour) Skeels, is a racemate. By means of the pure enantiomers of 4,5-disubstituted γ-butyrolactams (I), according to the invention, it is now possible to synthesize (+)-(3R),(4S),(5S),(7R)-3-hydroxy-5α-hydroxybenzyl-1-methyl-4-phenyl-pyrrolidin-2-one and derivatives in the form of pure enantiomers.

The reduction of the compound of the formula (II) to give compounds of the formula (X) in step [C] is carried out by the same method and under the same conditions as already described for the reduction of compounds (V) to give compounds (IIb).

The oxidation of compounds of the formula (X) to give compounds of the formula (III) in step [D] is carried out by the same method and under the same conditions as already described for the oxidation of compounds of the formula (IIa) to give compounds of the formula (V).

The starting compounds of the formula (VI) are known from the literature or can be prepared by methods which are known from the literature or can be prepared by methods which are known from the literature [G. H. Cocolas, W. H. Hartung, J. Am. Chem. Soc. 79, 5203 (1957); F. Zymalkowski, P. Pachaly, Chem. Ber. 100, 1137 (1967)].

In animal experiments (+)-clausenamide had a marked protective effect against cerebral hypoxia as well as a marked antiamnesic effect, these effects being significantly more powerful than those of piracetam which is the structurally most closely related compound in the field of cerebral therapeutics and nootropics.

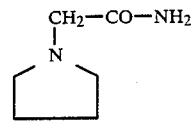

Piracetam

At high dosages animals did not display any significant changes in behaviour. The effect of the protection against hypoxia is thus evidently not caused by nonspecific sedation, which would produce a reduced oxygen requirement.

It was found that the acute toxicity of the compound is very low.

The present invention includes pharmaceutical formulations which contain the compound according to the invention in addition to non-toxic, inert, pharmaceutically suitable excipients or which consist of the active compound according to the invention, as well as processes for the preparation of these formulations.

Non-toxic, inert, pharmaceutically suitable excipients are to be understood as being solid, semi-solid or liquid diluents, fillers or formulation auxiliaries of all kinds.

The preferred pharmaceutical formulations which may be mentioned are tablets, coated tablets, capsules, pills, granules, suppositories, solutions, suspensions and emulsions, pastes, ointments, gels, creams, lotions, powders and sprays.

Tablets, coated tablets, capsules, pills and granules can contin the active compound or compounds in addition to the customary excipients, such as (a) fillers and extenders, e.g. starch, lactose, sucrose, glucose, mannitol and silicic acid, (b) binders, e.g. carboxymethyl cellulose, alginates, gelatine, polyvinyl pyrrolidone, (c) humectants, e.g. glycerol, (d) disintegrants, e.g. agar-agar, calcium carbonate and sodium carbonate, (e) solution retarders, e.g. paraffin and (f) absorption accelerators, e.g. quarternary ammonium compounds, (g) wetting agents, e.g. cetyl alcohol, glycerol monostearate, (h) adsorbents, e.g. kaolin and bentonite and (i) lubricants, e.g. talcum, calcium and magnesium stearate and solid polyethylene glycols or mixtures of the substances listed under (a) to (i).

The tablets, coated tablets, capsules, pills and granules can be provided with the customary coatings and shells, optionally containing opacifying agents, and can also be of such composition that they release the active compound only, or preferentially, in a certain part of the intestinal tract, optionally in a delayed manner, it being possible to use, for examples, polymeric substances and waxes as embedging compounds.

The active compound can, optionally together with one or more of the above mentioned excipients, also be in a micro-encapsulated form.

In addition to the active compound suppositories can obtain the customary water-soluble or water-insoluble excipients, e.g. polyethylene glycols, fats, e.g. cocoa fat and higher esters, (e.g. $C_{14}$ alcohol with $C_{16}$ fatty acid) or mixtures of these substances.

Ointments, pastes, creams and gels can contain, in addition to the active compound, the customary excipients, e.g. animal and vegetable fats, waxes, paraffins, starch, tragacanth, cellulose derivatives, polyethylene glycols, silicones, bentonites, silicic acid, talcum and zinc oxide or mixtures of these substances.

Powders and sprays can contain in addition to the active compound, the customary excipients, e.g. lactose, talcum, silicic acid, aluminium hydroxide, calcium silicate and polyamide powder or mixtures of these substances. Sprays can additionally contain the customary propellants, e.g. chlorofluorohydrocarbons.

Solutions and emulsions can contain, in addition to the active compound, the customary excipients such as solvents, solubilisers and emulsifiers, e.g. water, ethyl alcohol, isopropyl alcohol, ethyl carbonate, ethyl acetate, benzyl alcohol, dimethyl formamide, benzyl alcohol, dimethyl formamide, oils, in particular cottonseed oil, peanut oil, maize germ oil, olive oil, cactor oil and sesame oil, glycerol, glycerol formal, tetahydrofurfuryl alcohol, polyethylene glycols and fatty acid esters of sorbitan or mixtures of these substances.

For parenteral administration the solutions and emulsions can also be present in a sterile and blood-isotonic form.

Suspensions can contain, in addition to the active compound, the customary excipients such as liquid diluents, e.g. water, ethyl alcohol, propylene glycol, suspending agents, e.g. ethoxylated isostearyl alcohols, polyoxyethylene sorbitol, and sorbitan esters, microcrystalline cellulose, aluminium metahydroxide, bentonite, agar-agar and tragacanth or mixtures of these substances.

The above mentioned formulation forms can also contain colouring agents, preservatives as well as smell- and taste-improving additives, e.g. peppermint oil and eucalyptus oil and sweetening agents, e.g. saccharin.

The therapeutically active compound should preferably be present in the above mentioned pharmaceutical formulations in a concentration of about 0.1 to 99.5, preferably about 0.5 to 95 percent by weight of the total mixture.

The above mentioned pharmaceutical formulations can also contain further pharmaceutical active compounds in addition to the compound according to the invention.

The above mentioned pharmaceutical formulations are prepared in the customary manner by known methods, e.g. by mixing the active compound or compounds with the excipient or excipients.

In the case of intravenous administration it has in general proven advantageous to administer quantities of about 0.001 to 1 mg/kg, preferably about 0.01 to 0.5 mg/kg of body weight in order to achieve effective results and in the case of oral administration the dosage is about 0.01 to 20 mg/kg, preferably 0.1 to 10 mg/kg of body weight.

Nevertheless, it may possibly be necessary to deviate from the stated quantities as a function of the body weight and the nature of the administration route, the individual reaction towards the medicament, its formulation and the time or interval at which it is administered. Thus in some cases it may be sufficient to use less than the above mentioned minimum quantity whereas in other cases the above mentioned upper limit must be exceeded. Where greater quantities are administered it may be recommendable to divide them into general individual administrations over the course of the day.

Using compounds of the formula I which have the (4R),(5R)-configuration and which can be prepared from compounds II having the (6S),(3R),(1'R)-configuration as the starting material, (−)-(3S),(4R),(5R),(7S)-3-hydroxy-5-α-hydroxybenzyl-1-methyl-4-phenyl-pyrrolidin-2-one is obtained.

Thus, for example, the synthesis of (+)-(3S),(4R),(5R),(7S)-3-hydroxy-5-α-hydroxybenzyl-1-methyl-4-phenylpyrrolidin-2-one from the (4S,5S)-5-methoxycarbonyl-4-phenyl-pyrrolidin-2-one according to the invention, prepared as described, can be carried out in accordance with the following equations:

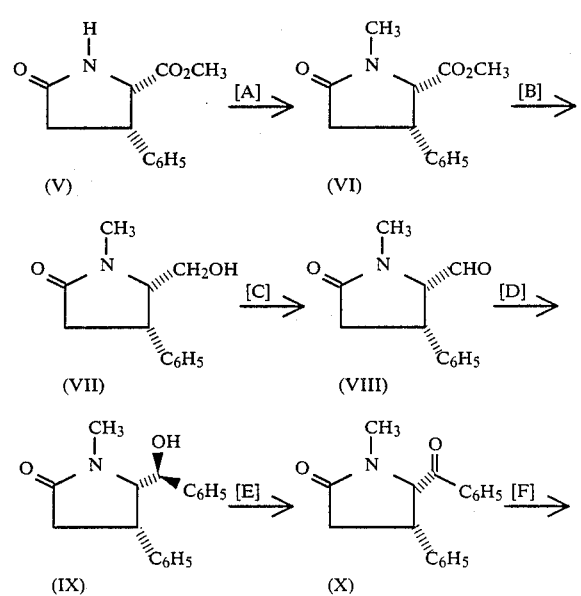

13

-continued

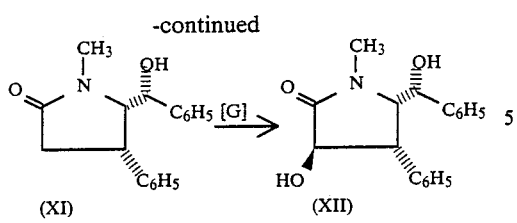

(XI)  (XII)

Accordingly, in step [A], (4S,5S)-5-methoxycarbonyl-4-phenyl-pyrrolidin-2-one (V) is methylated with a methylating agent such as, for example, methyl bromide, methyl iodide, methyl p-toluene sulfonate, diazomethane or dimethylsulfate if appropriate in the presence of a base such as sodium, sodium hydride, sodium amide, butyllithium or lithium diisopropylamide, in suitable solvents such as diethyl ether, tetrahydrofuran, dimethylformamide, hexamethylphosphoric acid triamide or mixtures of the solvents, at temperatures from −20° C. to +80° C., preferably from 0° C. to +40° C. Particularly preferably, the methylation in step [A] is carried out with methyl iodide in a mixture of tetrahydrofuran and hexamethylphosphoric acid triamide in the presence of lithium diisopropylamide as the base.

The reduction of (VI) to (4S,5S)-5-hydroxymethyl-1-methyl-4-phenylpyrrolidin-2-one (VII) in step [B] is preferably carried out with complex metal hydrides such as, for example, lithium hydrido-triethyl borate, lithium hydrido-tris-(1-methylpropyl) borate or sodium borohydride in inert solvents such as ethers, for example diethyl ether, tetrahydrofuran or dioxane, at temperatures from −30° C. to +10° C., preferably from −20° C. to 0° C.

The oxidation of (VII) to (4S,5S)-5-formyl-1-methyl-4-phenyl-pyrrolidin-2-one (VIII) in step [C] is carried out with dimethyl sulfoxide as the oxidizing agent, with the addition of trifluoroacetic anhydride in chlorohydrocarbons such as, for example, dichloromethane or chloroform, or in ethers such as diethyl ether, dioxane or tetrahydrofuran, at temperatures from −80° C. to 0° C., preferably from −60° C. to 0° C.

In step [D], the formyl compound (VIII) is reacted in suitable solvents such as an ether, for example diethyl ether or tetrahydrofuran, in a temperature range from −20° C. to +50° C., preferably from −10° C. to +30° C., with phenylmagnesium bromide to give (4S,5S,7S)-5-hydroxymethylphenyl-1-methyl-4-phenylpyrrolidin-2-one (IX).

The oxidation of (IX) to (4S,5S)-5-benzoyl-1-methyl-4-phenylpyrrolidin-2-one (X) in step [E] is carried out under the same conditions as already indicated for the oxidation of (VII) to (VIII) in step [C].

The reduction of (X) to (4S,5S,7R)-5-hydroxymethylphenyl-1-methyl-4-phenylpyrrolidin-2-one (XI) in step [F] is carried out under the same conditions as already described for the reduction of (VI) to (VII) in step [B].

The hydroxylation of (XI) to (3R,4S,5S,7R)-3-hydroxy-5-hydroxymethylphenyl-1-methyl-4-phenylpyrrolidin-2-one [(+)-Clausen amide] (XII) described in step [G] is carried out with an oxidizing agent, such as molybdenum peroxide/pyridine or oxygen in the presence of phosphites, such as trialkyl phosphites, for example trimethyl phosphite, triethyl phosphite or tripropyl phosphite, and in the presence of bases, for example metal-organic bases, such as lithium diisopropylamide or butyllithium in inert organic solvents, such as ethers, for example diethyl ehter or tetrahydrofuran, or hexamethylphosphoric acid triamide or mixtures thereof, in a temperature range from −80° C. to 0° C.

PREPARATION EXAMPLES

Example 1

(3S,6R,1'S)-2,5-Dimethoxy-6-isopropyl-3-[2'-methoxycarbonyl-1'-phenyl]-ethyl-3,6-dihydro-1,4-pyrazine

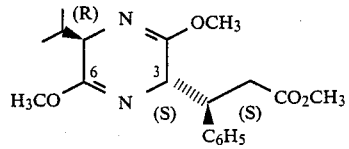

The solution of 20 g (108.4 mmol) of (3R)-2,5-dimethoxy-3-isopropyl-3,6-dihydro-1,4-pyrazine in 120 ml of absolute tetrahydrofuran was cooled to −70° C. and, under an N₂ atmosphere, 70 ml (108.4 mmol) of a 1.6N solution of n-butyllithium in hexane were added. The mixture was stirred for 10 minutes at this temperature, and a solution of 19.36 g (119.2 mmol) of methyl cis-cinnamate in 60 ml of absolute THF was added. The mixture was stirred for 12 hours at −70° C. and for 1 hour at −20° C., 6.83 ml (108.4 mmol) of glacial acetic acid dissolved in 10 ml of absolute THF were added, and the reaction mixture was allowed to come to room temperature and poured onto 300 ml of ice water. This was extracted with three times 150 ml of ethyl acetate, the combined organic extracts were dried over MgSO₄ and filtered, and the solvent was stripped off in vacuo. This gave 33.1 g (88% of theory), of the crude title compound as a light yellow oil. Flash chromatography on silica gel (Amicon, particle size 20–45 μm; eluent: toluene/ethyl acetate=20/1) gave, in addition to 4.9 g (13% of theory) of the 6R,3S,1'R-isomer [R$_f$(toluene:ethyl acetate=9:1)=0.36], 27.4 g (73% of theory) of the pure title compound having R$_f$(toluene:ethyl acetate=9:1)=0.46 as a pale yellow oil. ¹H-NMR (CDCl₃, 250 MHZ): δ=0.57 and 0.89 (each d, J=6.9 Hz, (CH₃)₂C, 2H); 2.1 (m; (CH₃)₂CH, 1H); ABM signal (δ$_A$=2.91, δ$_B$=3.18, J$_{AB}$=15.6 Hz, J$_{AM}$=J$_{BM}$=6.8 Hz, 2H, 2'-H); 3.08 (t, J=3.1 Hz, 1H, C(3)-H); 3.61, 3.65 and 3.72 (each s, each 3H, OCH₃); 3.9 (dt, J=6,8 Hz, J=3.1 Hz, 1H, C(1')-H); 4.34 (t, J=3.1 Hz, 1H, C(6)-H); 7.0–7.25 (m, 5H, aromatic H).
MS; M+ 347
C₁₉H₂₆N₂O₄ (346.4) Calculated: C 65.9; H 7.6; N 8.1
Found: C 66.5; H 7.7; N 8.0

Example 2

(4S,5S)-5-Methoxycarbonyl-4-phenylpyrrolidin-2-on

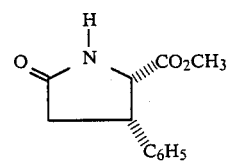

13.7 g (39.5 mmol) of the compound from Example 1 were vigorously stirred in 317 ml of 0.25N hydrochloric acid for 48 hours. The mixture was extracted with three time 100 ml of diethyl ether (recovery of starting material). The aqueous solution was lyophilized, and the remaining residue was suspended in 5 ml of water and adjusted to pH=10 with about 2.8 ml of concentrated ammonia. The mixture was extracted with five times 100 ml of ethyl acetate, with addition of NaCl up to saturation, and dried over MgSO₄, and the solvent was stripped off in vacuo. The crude amino acid ester mixture was held at 100° C./0.1 mm Hg for 10 hours in a bulb tube. 5 g (58% of theory) of the title compound having $[\alpha]_D^{20}=209.05$ (c=0.54, MeOH); $R_f=0.20$ (ethyl acetate), were obtained as the residue.

¹H-NMR (CDCl₃, 200 mHz): δ=2.78 (dd, J=7.5 Hz, J=2 Hz, 2H, C(3)-H); 3.30 (s, 3H, OCH₃); 3.99 (q, J=7.5 Hz, 1H, C(4)-H); 4.58 (d, J=7.5 Hz, 1H, C(5)-H); 6.85 (br, 1H, NH); 7.19–7.35 (m, 5H, C₆H₅).

(C₁₂H₁₃NO₃, 219.24) Calculated: C 65.7; H 6.0; N 6.4 Found: C 65.5; H 6.1; N 6.4

Example 3

(4S,5S)-N-Methyl-5-methoxycarbonyl-4-phenylpyrrolidin-2-one

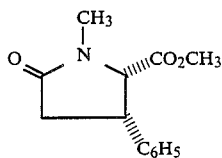

5 g (22.8 mmol) of the title compound of Example 2 were dissolved in 50 ml of absolute tetrahydrofuran and 15 ml of absolute hexamethylphosphoric acid triamide in a dry flask, dried 1 with a gas burner, under an N₂ atmosphere and cooled to −70° C. At this temperature, the solution of 25.1 mmol of lithium diisopropylamide in THF/hexane (prepared from 15.7 ml of 1.55 N Buli in hexane and 3.5 ml of diisopropylamine, in 15 ml of THF) was added dropwise, the mixture was stirred for a further 20 minutes at this temperature, the solution of 4.2 ml (0.114 mol) of methyl iodide in 5 ml of absolute THF was added dropwise, and the mixture was stirred for 1 hour at −70° C. and allowed to come to room temperature in the course of 30 minutes. As soon as all the starting material had been reacted (DC check), the reaction mixture was poured onto 200 ml of phosphate buffer (pH=7, pH check) and extracted with four times 100 ml of ethyl acetate (finally with addition of sodium chloride). Drying (MgSO₄) and evaporation in a rotary evaporator gave the crude title compound, which was filtered with ethyl acetate over silica gel. This gave 5.05 g (94.6% of theory) of the pure title compound as a colorless solid having $R_f=0.3$ (ethyl acetate) and $[\alpha]_D^{20}=205.95$ (c.=0.38, MeOH) and melting point: 100° C.

IR (KBr): $\nu=1736, 1690 \text{ cm}^{-1}$

¹H-NMR (250 MHz, CDCl₃): δ=ABX signal (δ=2.70, δ_B=2.95, J_{AB}=17.5 Hz, J_{AX}=10 Hz, J_{BX}=11 Hz, 2H, C(3)-H); 2.89 (S, 3H, N-CH₃); 3.30 (s, 3H, OCH₃); 3.91 (q, J=10 Hz, 1H, C(4)-H); 4.39 (d, J=9–10 Hz, 1H, C(5)-H); 7.18–7.38 (m, 5H, C₆H₅).

C₁₃H₁₅NO₃ (233.27) Calculated: C 66.9; H 6.5; N 6.0 Found: C 67.1; H 6.5; N 6.0

Example 4

(4S,5S)-5-Hydroxymethyl-1-methyl-4-phenylpyrrolidin-2-one

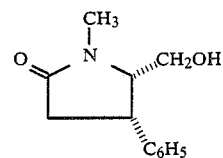

25.6 mmol of LiB(Et)₃H (as a 1 M solution in THF, 25.6 ml) were added dropwise at −15° to −20° C. under an N₂ atmosphere to the solution of 3 g (12.8 mmol) of the title compound from Example 3 in 33 ml of absolute tetrahydrofuran. The mixture was stirred for a further 1 hour at −20° C. and 1 hour at 0° C., and the reaction mixture was poured into about 200 ml of icecold 2N hydrochloric acid, vigorously stirred for 30 minutes and extracted with twice 200 ml of ethyl acetate. The aqueous phase was saturated with sodium chloride and extracted again with twice 200 ml of ethyl acetate. The collected organic extracts were washed with a little water, dried over MgSO₄ and evaporated in a rotary evaporator. The residue was caused to crystallize by means of a little ether and then precipitated with pentane, until turbidity at the dropping-in point was no longer observable. After filtering off with suction and drying, this gave 2.07 g (79% of theory) of the title compound having the melting point: 93°–95° C.

IR (KBr): $\nu=3324, 1687 \text{ cm}^{-1}$.

¹H-NMR CDCl₃, 300 MHz): δ=AB part of ABM system, δ_A=2.59, δ_B=2.97 (each dd, J_{AB}=15 Hz, J_{AM}=7.5 Hz, J_{BM}=9 Hz, 2H, C(3)-H); 2.97 (s, 3H, N-CH₃); AB part of ABM system, δ_A=3.36, δ_B=3.62 (each dd, J_{AB}=11.2 Hz, J_{AM=JBM}=3 hz, 2H, C(7)-H); 3.72–3.85 (m, 2H, C(4)-H, C(5)-H); 7.32 (m, 5H, C₆H₅).

C₁₂H₁₅NO₂ (205.26) Calculated: C 70.2; H 7.4; N 6.8 Found: C 70.0; H 7.4; N 6.8

Example 5

(4S,5S)-5-Formyl-1-methyl-4-methyl-4-phenylpyrrolidin-2-one

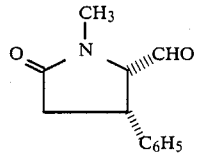

The solution of 2.97 ml of trifluoroacetic anhydride in 5.6 ml of absolute dichloromethane was added dropwise to the solution of 1.9 ml (28 mmol) of absolute dimethyl sulfoxide in 14 ml of absolute dichloromethane under an N₂ atmosphere in the course of 10 minutes at −60° C. The mixture was stirred for 15 minutes at this temperature and the solution of 2.9 g (14 mmol) of the title compound from Example 4 in 25 ml of dichloromethane was added dropwise in such a way that the temperature did not exceed −60° C. Stirring was continued for 90 minutes at −60° C., and the mixture was warmed briefly to −30° C. (5–10 minutes) and cooled down agin to 31 60° C. At this temperature, 5.6 ml of absolute triethylamine were added slowly, the mixture was stirred for 30 minutes at −60° C. and warmed to room temperature. 60 ml of water were added, the phases were separated, and the aqueous phase was extracted with three times 25 ml of dichloromethane. The collected organic extracts were washed with twice 300 ml of water, dried over magnesium sulfate and evaporated in a rotary evaporator. This gave 2.83 g (100% of theory) of the title compound having $R_f=0.25$ (ethyl acetate) (91% pure according to the $^1$H-NMR spectrum). After drying (24 hours, high vacuum), the crude product thus obtained was directly reacted further.

IR (CHCl$_3$) $\nu=1734$, 1689 cm$^{-1}$ $^1$H-NMR (300 MHz, CDCl$_3$): $\delta=2.79$ (dd, J=5.3 Hz, J=9.7 Hz, 2H, C(3)-H); 2.91 (s, 3H, N-CH$_3$); 4.02 (q, J=9.7 Hz, 1H, C(4)-H); 4.30 (dd, J=1 Hz, J=9.7 Hz, 1H, C(5)-H); 7.3 (m, 5H, C$_6$H$_5$); 9.17 (d, J=1 Hz, 1H, CHO).

Example 6

(4S,5S,7S)-5-Hydroxymethylphenyl-1-methyl-4-phenylpyrrolidin-2-one

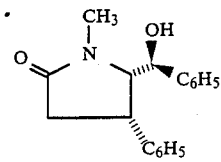

The solution of 2.48 g (1.67 ml, 0.0156 mol) of bromobenzene in 4.4 ml of absolute tetrahydrofuran was added dropwise under N$_2$ to 0.39 g of Mg filings in such a way that the THF boiled gently. 10 ml of absolute THF were then added, and the mixture was heated to the boil under reflux until all the magnesium was dissolved (1-2 hours).

The solution was cooled to 0° C. and, with vigorous stirring the solution of 2.47 g (0.012 mol) of the title compound from Example 5 in 25 ml of absoulte THF was added dropwise in such a way that the temperature did not exceed 5° C. In some cases it was necessary to add absolute THF in order to improve stirrability. The reaction mixture was then stirred for 1 hour at 0°-5° C., poured onto 35 ml of 0.5 n HCl/ice and extracted with four times 30 ml of ethyl acetate and with twice 30 ml of dichloromethane. The collected ethyl acetate and dichloromethane extracts were washed (separately!) with twice 20 ml of water, combined and dried over magnesium sulfate. The residue remaining after stripping off the solvent (in vacuo) was triturated with 10 ml of ether until it crystallized. 50 ml of pentane were then added slowly, and the mixture was left to stand overnight in a refrigerator. Filtering off the solid with suction gave 2.5 g (74.3% of theory) of the title compound having Melting point: 210°-212° C.

$[\alpha]_D^{20}=173.1$ (c=0.5, MeOH)

IR (KBr): $\nu=3362$ (br), 1654 cm$^{-1}$ $^1$H-NMR (300 MHz, d$_6$-DMSO): $\delta=2.21$ (S, 3H, NCH$_3$); 2.24 (dd, A part of ABM system, $J_{AB}=15.7$ Hz, $J_{AM}=9.4$ Hz, 1H, cis-C(3)-H); 3.05; (dd, B part of ABM system, $J_{BM}=12.7$ Hz, 1H, trans-C(3)-H); 3.80 (dt, M part of ABM system, $J_{AM}=9.4$ Hz, $J_B=12.7$ Hz, $J_{4,5}=8.5$ Hz, 1H, C(4)-H); 4.15 (dd, J=8.5 hz, J=1 Hz, 1H, C(5)-H); 4.26 (dd, J=6 Hz, J=Hz, 1H, C(7)-H); 5.35 (d, J=6 Hz, 1H, OH); 7.15-7.5 (m, 10 H, C$_6$H$_5$).

C$_{18}$H$_{19}$NO$_2$ (281.4) Calculated: C 76.8; H 6.8 Found: C 76.5; H 6.8

Example 7

(4S,5S)-5-Benzoyl-1-methyl-4-phenylpyrrolidin-2-one

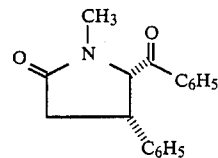

The solution of 1.8 ml of trifluoroacetic anhydride in 34 ml of absolute dichloromethane was added dropwise to the solution of 1.2 ml (0.0171 mol) of absolute dimethyl sulfoxide in 8.7 ml of absolute dichloromethane under an N$_2$ atmosphere in the course of 10 minutes at −60° C. The mixture was stirred for a further 15 minutes at this temperature and the solution of 2.4 g (0.0085 mol) of the title compound from Example 6 in about 70 ml of absolute dichloromethane was added dropwise in such a way that the temperature did not exceed −60° C. Stirring was continued for 90 minutes at −60° C., and the mixture was warmed briefly to −30° C. (9-10 minutes) and cooled down again to −60° C. At this temperature, 3.4 ml of triethylamine were added slowly, and the mixture was stirred for 20 minutes at −60° C. and warmed to room temperature. "ml of water were added, the phases were separated and the aqueous phase was extracted with three times 25 ml of dichloromethane. The combined organic extracts were washed with twice 30 ml of water, dried over magnesium sulfate and evaporated in a rotary evaporator. The residue was evaporated in the rotary evaporator with twice 20 ml of ether. This gave 2.3 g (100% of theory) of the title compound as a solid having a melting point: 115°-116° C. and $R_f=0.25$ (ethyl acetate). The crude product, which was pure according to the $^1$H-NMR spectrum, was directly reacted further.

IR (KBr): $\nu=1695$, 1682 cm$^{-1}$ $^1$H-NMR (300 MHz, CDCl$_3$): $\delta=2.78$ and 2.91 (AB part of ABM spectrum, $J_{AB}=16.5$ Hz, $J_{AM}=J_{BM}=8.3$ Hz, 2H, c(3)-H); 2.88 (s, 3H, N-CH$_3$); 4.02 (q, J=8.3 Hz, 1H, C(4)-H); 5.42 (d, J=8.3 Hz, 1H, C(5)-H); 7.0, 7.21, 7.59. 7.50 (each m, 10H, C$_6$H$_5$).

Example 8

(4S,5S,7R)-5-Hydroxymethylphenyl-1-methyl-4-phenylpyrrolidin-2-one

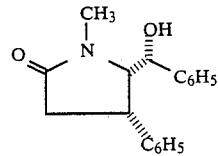

8.3 mmol of Li B(Et)$_3$I (8.3 ml of a 1M solution in THF) were added dropwise at −15° C. to −20° C. under an N$_2$ atmosphere to the solution of 2.3 g (8.2 mmol) of the title compound from Example 7 in 20 to 27 ml of absolute tetrahydrofuran. The mixture was stirred for a further 1 hour at 0° C., and the reaction mixture was poured into 10 ml of ice-cold 1N HCl and extracted with twice 20 ml of ethyl acetate. The aqueous phase was saturated with sodium chloride and extracted again with twice 20 ml of ethyl acetate. The combined organic extracts were dried over MgSO$_4$ and evaporated in the rotary evaporator. The residue was dissolved in dichloromethane and washed with twice 10 ml of water. The organic phase was dried (MgSO$_4$) and evaporated in the rotary evaporator. The residue was caused to crystallize by means of 10 ml of ether, and pentane was then slowly added with stirring, until turbidity at the dropping-in point was no longer observable.

The precipitate was filtered off with suction and dried. This gave 1.6 g (72% of theory) of the title compound having a melting point: 189°–195° C. According to $^1$H-NMR, the product is 95% pure, and it was directly reacted further.

For analysis, it was recrystallized from acetone (melting point: 197°–8° C.).

IR (KBr): $\nu$=3251, 1692 cm$^{-1}$.

$^1$H-NMR (300 MHz, DMSO): $\delta$=1.97 and 2.05 (ABM signal, B $J_{AB}$=13.5 Hz, $J_{AM}$=8.2 Hz, $J_{BM}$=13 Hz, 2H, C(3)-H); 2.91 (s, 3H, N-CH$_3$); 3.82 (dt, $J_{AM}$=J$_{4,5}$=8.2 Hz, $J_{BM}$=13 Hz, 1H, C(4)-H); 4.27 (dd, J=8.2 Hz, J=1.5 Hz, 1H, C(5)-H); 4.65 (dd, J=1.5 Hz, J=3.5 Hz, 1H, C(7)-H); 5.34 (d, J=3.5 Hz, 1H, C-(7)-OH); 6.70, 7.11, 7.25 (each m, 10H, C$_6$H$_5$).

C$_{18}$H$_{19}$NO$_2$ (281.4) Calculated: C 76.8; H 6.8; N 5.0 Found: C 77.0; H 6.9; N 5.0

Example 9

(3R,4S,5S,7R)-3-hydroxy-5-hydroxymethylphenyl-1-methyl-4-phenylpyrrolidin-2-one[(+)-Clausen amide]

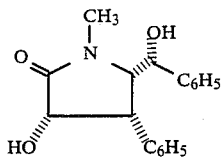

The solution of 0.44 g (1.57 mmol) of the title compound from Example 8 in 12.25 ml of absolute tetrahydrofuran and 3.25 ml of absolute hexamethylphosphoric acid triamide was placed into a flask, dried in vacuo and blanketed with high-purity nitrogen, and cooled to −70° C. At this temperature, the solution of 0.0038 mol of lithium diisopropylamide in 4.5 ml of absolute THF/hexane (prepared from 0.553 ml of diisopropylamine in 2 ml of THF by addition of 2.6 ml of a 1.5N solution of n-butyllithium in hexane at −20° C. to 0° C.) was added dropwise. The mixture was stirred for a further 1 hour at −70° C. to −60° C., 0.13 ml of freshly distilled trimethyl phosphite (dissolved in a little absolute tetrahydrofuran) was added and absolute oxygen (dried over H$_2$SO$_4$ and P$_4$O$_{10}$) was introduced (50–100 ml/minute). As soon as the ratio of (product/starting material) no longer changed (2–3 hours) according to a DC check (SiO$_2$; EA/MeOH: 2/1; R$_f$=0.3 for the title compound and R$_f$=0.37 for the starting material, dyeing with molybdatophosphoric acid spray reagent from Messrs. Merck, Darmstadt), the mixture was poured onto 15 ml of 0.5N HCl while cooling with ice and, if necessary, acidified to pH 3 to pH 4.

The phases were separated and the aqueous phase was extracted with four times 10 ml of ethyl acetate. The combined organic extracts were washed with three times 10 ml of water, dried over MgSO$_4$ and evaporated in a rotary evaporator. The residue was taken up in 5–10 ml of ether and stirred until crystallization started, and quantities of pentane were added slowly with stirring until turbidity at the dropping-in point was no longer observable. The mixture was left to stand overnight in the refrigerator and filtered with suction. This gave about 0.4 g of a crude solid which, in addition to the title compound, contained about 35–40% of starting material. For purification, it was recrystallized twice from methanol. The title compound is then obtained in about 95% purity. Chromatography over alumina (neutral) proceeds with less loss and with recovery of the pure starting material. For this purpose, the crude product is adsorbed on silica gel (dissolving in warm MeOH, addition of five parts by weight of silica gel, evaporation in a rotary evaporator and several further evaporations with ethyl acetate in a rotary evaporator, until a dust-dry MeOH-free product results). The adsorbate is charged to a column with Al$_2$O$_3$ (neutral, 50 parts by weight) and the starting material is eluted first with ethyl acetate (flash chromatography, check with DC and analytical HPLC). The title compound is then eluted with ethyl acetate/methanol mixtures (40/1, 20/1 and then 10/1). Crystallization was initiated with ether, the crystals were thoroughly stirred with water and filtered off with suction, and after drying in a high vacuum (30°–40° C., 24 hours) 0.22 g (46.1% of theory) of (+)-Clausen amide (the hydrate contains a ¼ mol of H$_2$O) with 236°–7,5° C. (authentic (±)-Clausen amide: 236°–7° C.) was obtained. Purity about 98% (according to $^1$H-NMR, it contains about 2% of starting material). It was possible to recover 0.1 g of the pure starting material. [$\alpha$]$^{20}$=+123.19 (C=0.46, DMSO/H$_2$O=9/1% by volume)

IR (KBr): $\nu$=3402, 3321, 1689 cm$^{-1}$.

1H-NMR 8300 MHz, DMSO): $\delta$=3.01, (s, 3H, N-CH$_3$); 3.50 (dd, J=8 Hz, J=10.5 Hz, 1H, C(4)-H); 3.82 (dd, J=10 Hz, J=7 Hz, 1H, C(3)-H); 4.30 (dd, J=8 Hz, J=2 Hz, 1H, C(5)-H); 4.65 (dd, J=2 Hz, J=3 Hz, 1H, C(7)-H); 5.39 (d, J=7 Hz, 1H C(3)-OH); 5.45 (d, J=3 Hz, 1H, C(7)-OH); 6.61–6.64 (m, 2H, aromatic H); 7.03–7.28 (m, 8H, aromatic H).

C$_{18}$H$_{19}$NO$_3$+¼H$_2$O (315.37) Calculated: C 71.6; H 6.5 Found: C 71.6; H 6.4

What is claimed is:

1. A Pure enantiomer of a 4,5-disubstituted$\alpha$-butyrolactam of the formula

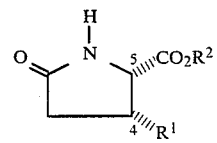

in which

R$^1$ represents aryl which has 6 to 14 carbon atoms and which is unsubstituted or mono or di substituted by alkyl, alkoxy, and alkylthio each having up to 8 carbon atoms; aryl, aryloxy and arylthio each having 6 to 12 carbon atoms, aralkyl having 7 to 14 carbon atoms, halogen, trifluoromethyl, trifluoromethoxy, difluoromethoxy, trifluoromethylthio, nitro, cyano, carboxyl, alkoxycarbonyl having up to 8 carbon atoms, sulfo; phenylsulfonyl, tolylsulfonyl, alkylsulfonyl having up to 8 carbon atoms, hydroxyl or a group of the formula

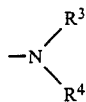

wherein
R³ and R⁴ each independently denote hydrogen, alkyl having up to 8 carbon atoms, aryl having 6 to 12 carbon atoms, aralkyl having 7 to 14 carbon atoms, ethylcarbonyl; benzoyl; acetyl; alkylsulfonyl having up to 6 carbon atoms, phenylsulfonyl or tolysulfonyl,
or represents
straight-chain, branched or cyclic saturated or unsaturated alkyl or alkenyl which has up to 10 carbon atoms and which is unsubstituted or substituted by halogen; aryl having 6 to 14 carbon atoms; hydroxyl; alkoxy and alkylthio each having up to 6 carbon atoms, carboxyl, alkoxycarbonyl having up to 6 carbon atoms; sulfo; alkylsulfonyl having up to 6 carbon atoms; phenylsulfonyl; tolysulfonyl or a group of the formula

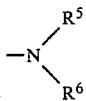

wherein
R⁵ and R⁶ each independently denote hydrogen, alkyl having up to 8 carbon atoms; aryl having 6 to 12 carbon atoms; aralkyl having 7 to 14 carbon atoms; ethylcarbonyl; benzoyl; acetyl; alkylsulphonyl having up to 6 carbon atoms; phenyl-sulfonyl or tolylsulfonyl,
and R² represents straight-chain, branched or cyclic alkyl having up to 8 carbon atoms, and in which the ring carbon atoms at the 5-position has the S-configuration and wherein the substituent R¹ in the 4-position has the cis-configuration relative to the substitutent COOR² in the 5-position.

2. A compound according to claim 1,
in which
R¹ represents phenyl or naphthyl which is unsubstituted or mono- or di- substituted by alkyl and alkoxy each having up to 6 carbon atoms; methylthio; phenyl; phenoxy; benzyl; fluoro; chloro; bromo; iodo; trifluoromethyl; trifluoromethoxy, difluoromethoxy; trifluoromethylthio, nitro; cyano; alkoxycarbonyl having up to 6 carbon atoms; phenylsulfonyl; tolysulfonyl; alkylsulfonyl having up to 6 carbon atoms, hydroxyl and a group of the formula

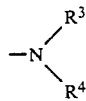

in which
R³ and R⁴ each independently denote hydrogen, alkyl, having up to 6 carbon atoms; phenyl; benzyl; acetyl; ethylcarbonyl; benzoyl; alkylsulfonyl having up to 4 carbon atoms; tolylsulfonyl or phenylsulfonyl,
or represents
a straight-chain, branched or cyclic alkyl which has up to 8 carbon atoms and which is unsubstituted or substituted by fluoro, chloro, bromo, phenyl, hydroxyl, alkoxy or alkylthio having up to 4 carbon atoms, alkoxycarbonyl having up to 4 carbon atoms, alkylsulfonyl having up to 4 carbon atoms, phenylsulfonyl, tolylsulfonyl or by a group of the formula

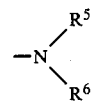

wherein
R⁵ and R⁶ each independently denote hydrogen; alkyl having up to 6 carbon atoms; phenyl; benzyl; acetyl; ethylcarbonyl; benzoyl; alkylsulfonyl having up to 4 carbon atoms; trolylsulfonyl or phenylsulfonyl,
and R² represents straight-chain or branched alkyl having up to 6 carbon atoms, and in which the ring carbon atom at the 5-position has the S-configuration and in which the substituent R¹ in the 4-position has the cis-configuration relative to the substituents COOR² in the 5-position.

3. A compound according to claim 1,
in which
R¹ represents phenyl which is unsubstituted or mono or di-substituted by alkyl or alkoxy having up to 4 carbon atoms, by fluoro, chloro, bromo, trifluoromethyl, trifluoromethoxy, trifluoromethylthio, nitro, cyano, alkoxycarbonyl having up to 4 carbon atoms, phenylsulfonyl, tolylsulfonyl, alkylsulfonyl having up to 4 carbon atoms, hydroxyl or by a group of the formula

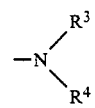

in which
R³ and R⁴ each independently denote hydrogen; alkyl having up to 4 carbon atoms; phenyl; benzyl or acetyl,
or represents straight-chain, branched or cyclic alkyl which has up to 6 carbon atoms which is unsubstituted or substituted by fluoro, chloro, bromo, phenyl, thienyl, pyridyl, furyl or alkoxy having up to 4 carbon atoms
and
R² represents straight-chain or branched alkyl having up to 4 carbon atoms, and in which the ring carbon atoms at the 5-position has the S-configuration and in which the substitutent R¹ in the 4-position has the cis-configuration relative to the substituent COOR² in the 5-position.

4. (+)-(3R,4S,5S,7R)-3-Hydroxy-5-hydroxymethylphenyl-1-methyl-4-phenylpyrrolidin-2-one.

5. A medicament useful in protecting a patient from hypoxia or as an antiamnestic agent comprising an effective amount of a compound according to claim 4.

* * * * *